United States Patent [19]
Miyashita

[11] Patent Number: 5,233,981
[45] Date of Patent: Aug. 10, 1993

[54] HOT COMPRESS STRUCTURE

[75] Inventor: Eiji Miyashita, Kanagawa, Japan

[73] Assignees: Ferric Inc.; Mitsui Toatsu Chemicals, Inc., both of Tokyo, Japan

[21] Appl. No.: 730,376

[22] Filed: Jul. 11, 1991

Related U.S. Application Data

[63] Continuation of Ser. No. 392,928, Aug. 2, 1989, filed as PCT/JP88/00447, May 6, 1988, abandoned.

[30] Foreign Application Priority Data

Dec. 7, 1987 [JP] Japan .................. 62-307625

[51] Int. Cl.⁵ .............................................. A61F 7/00
[52] U.S. Cl. ...................... 607/114; 126/263
[58] Field of Search ................... 128/399–403; 126/263, 204; 44/250–253

[56] References Cited

U.S. PATENT DOCUMENTS

| | | | |
|---|---|---|---|
| 3,865,117 | 2/1975 | Perry | 126/263 |
| 3,889,684 | 6/1975 | Lebold | 128/402 |
| 3,976,049 | 8/1976 | Yamashita et al. | 126/263 |
| 4,114,591 | 9/1978 | Nakagawa | 126/263 |
| 4,366,804 | 1/1983 | Abe | 126/263 |
| 4,516,564 | 5/1985 | Koiso et al. | 126/263 |
| 4,522,190 | 6/1985 | Kuhn et al. | 126/263 |
| 4,736,088 | 4/1988 | Bart | 128/402 |
| 4,756,299 | 7/1988 | Podella | 126/263 |

FOREIGN PATENT DOCUMENTS

| | | |
|---|---|---|
| 627472 | 2/1981 | Japan . |
| 5937147 | 8/1982 | Japan . |
| 58-92752 | 6/1983 | Japan . |
| 92752 | 6/1983 | Japan . |
| 37147 | 2/1984 | Japan . |
| 62-217961 | 3/1986 | Japan . |
| 61-268251 | 11/1986 | Japan . |
| 7472 | 2/1987 | Japan . |
| 62-183759 | 8/1987 | Japan . |
| 183759 | 8/1987 | Japan . |
| 217961 | 9/1987 | Japan . |

Primary Examiner—Mark S. Graham
Attorney, Agent, or Firm—Scully, Scott, Murphy & Presser

[57] ABSTRACT

A hot compress structure comprising a flat bag having no opening and having one surface constituted by a gas-permeable film, and a heating composition capable of generating heat in the presence of air and sealed in the interior of the flat bag, with a compress layer being provided on the other surface side of the flat bag, the gas-permeable film having a moisture permeability of 100 to 400 g/m².24 hr as measured according to an ASTM method (E-96-80D method). When this hot compress structure is brought into close contact with the human body, the heat generated from the heating composition is transferred to the whole skin surface of an affected part uniformly through the compress layer and a safe temperature not causing a low-temperature burn is maintained for a long time; besides, by the generation of heat, a local blood circulation is accelerated to improve a local metabolism.

10 Claims, 4 Drawing Sheets

HOT COMPRESS STRUCTURE

This application is a continuation of application Ser. No. 07/392,928, filed on Aug. 2, 1989, filed as PCT/JP88/00447, May 6, 1988, abandoned.

BACKGROUND OF THE INVENTION

1. Field of the Invention

The present invention relates to a hot compress structure and more particularly to a hot compress structure which when brought into close contact with the human body permits the heat of a heating composition to be transferred to the skin uniformly throughout the whole surface of the skin through a compress layer and which is capable of maintaining a safe temperature, not causing a low-temperature burn, for a long time and further capable of promoting local blood circulation by the generation of heat to improve local metabolism.

2. Discussion of the Prior Art

Hot compresses are used as means for treating symptoms involving local stiffness, pain and cold such as, for example, stiffness in the shoulder, muscle pain, cold hands and feet, neuralgia, rheumatism and lumbago. According to the conventional treating method of using a hot stupe, the following may be applied directly to an affected part: a towel or konnyaku jelly (a paste made from the starch of the devil's tongue), hot pack, paraffin bath, a fomentation containing a stimulative component such as cayenne-pepper extract, a disposable pocket heat, etc.

In the above-described conventional treating method of using a warmed towel or konnyaku jelly or a hot pack, there is reasonable concern that a burn could result from a high temperature or, conversely, the fomentation effect may not be obtained at a low temperature; further, a stuped condition will be obtained only for a short time because of an extremely poor retainability of a predetermined temperature at which the fomentation effect is obtained. It is further necessary to discontinue the daily activity during the treatment of this kind. Thus, various restrictions are involved in the use of conventional methods and so such treating method is deficient in simplicity.

Moveover, in the treatment using a warmed towel or konnyaku jelly, the heating source is not self-heating, so the heat will be removed by evaporation cooling from the fomentation with the lapse of time so the compress is cooled, thus having a reverse effect on the affected part.

Particularly in the case of a warmed towel or konnyaku jelly or a hot pack, it is troublesome to effect heating using boiling water or a heater, and when initially used they are so hot that it is required to use several towels or the like between them and the skin; besides, the temperature drops in a short time.

In the case of a paraffin bath, the place where it is to be used is limited and the regions to which it is to be applied are also restricted to hands and feet; further, staining of the skin is a problem, because of the use of oil.

As to a fomentation containing cayenne-pepper extract, it is said that the skin temperature is raised 1° to 2° C. by the stimulation of a peripheral sense of heat. And it is widely used because the method of using the same is easy. However, various problems are involved with the use of cayenne-pepper compresses such as, for example, rubefaction, eruption or skin poisoning caused by a stimulative component. Further, the skin feels a strong stimulation when the patient takes a bath after application of the compress on the skin. Thus, frequent use of such fomentation is dangerous.

In order to obtain a sufficient treating effect of a hot compress, the compress is sometimes required to have a durable heat retaining power at a certain constant temperature. For example, when a hot fomentation is used in close contact with the human body, it is sometimes required that the skin can be stuped over a long period of time at a certain constant skin temperature, more particularly, at a temperature not exceeding 44° C. at which the skin does not undergo a low-temperature burn. However, such durable heat retainability is not satisfied by any of the hot fomentation means referred to above.

Further, although a disposable pocket heater is easy to use, the temperature cannot be controlled to a satisfactory extent and hence a temperature exceeding a certain level can cause a low-temperature burn, even when it is brought into pressure contact with the skin surface through a buffer material such as cloth. The temperature transfers mostly at the portion of pressure contact, thus limiting the effectiveness of the heat.

Recently, in view of the above-mentioned problems, there has been proposed a hot compress structure comprising a disposable pocket heater and a fomentation as an integral structure (Japanese Patent Publication No. 13914/78). According to this proposal, a disposable pocket heater and the cloth surface of a fomentation with ointment spread thereon are stuck together and the ointment surface is brought into contact with an affected part, whereby the heat generated from a heating composition in the pocket heater is transferred to the skin surface through the compress layer of the hot compress structure.

The hot compress structure is very easy and convenient to use because all that is required is merely taking it out of a bag and applying it directly to an affected part. However, the following problems remain to be solved.

1. In the latter compress an air permeation layer comprising an air-permeable member and a perforated film, the perforated film having air-permeable holes at a ratio of 0.055–0.001 relative to the area of the hot compress structure is utilized. Therefore, the moisture permeation is as large as 2,000 $g/m^2.24$ hr as measured according to an ASTM method (E-96-80D method). The amount of oxygen permeated through the air permeation layer from the outside air is large and the amount of heat generated large, the resulting temperature exceeding 60° C. Further, since steam is released to the exterior of the system, the internal pressure of the bag containing the heating composition does not become high and the partial pressure oxygen is held at about 1/5 atmosphere like the outside air, so the heating temperature is maintained high.

2. Because of the heat generation at a high temperature, the vaporization of water is accelerated, and because of a large moisture permeation, the emanation of steam to the exterior of the system is vigorous. Consequently, the amount of water contained in the heating composition becomes small, so the oxidation of iron powder becomes insufficient and the duration of heat generation becomes short.

3. The perforated film used in the working examples of the foregoing patent publication has 3.0 mm dia. holes, so that the supply of oxygen is concentrated on those holes and heat is generated only therein, with no generation of heat in the other portion free of such holes. Thus, the temperature distribution becomes non-uniform.

4. Since the amount of moisture permeated through the perforated film is large, as mentioned in paragraph 1, the permeation of oxygen and steam can be done easily. Consequently, the internal pressure of the bag which contains the heating composition becomes approximately one atm.

As a result, the heating composition will move and be localized in the bag during use, thus causing variations in the temperature distribution of the hot compress structure, or causing a sense of incongruity at the applied part because the compress is applied directly to the user's skin. Such a sense of incongruity of the user can be eliminated by shaking the hot compress structure to make its temperature distribution uniform, but this is troublesome.

Because of the aforementioned drawbacks, hot compress structures proposed heretofore have not been put to practical use because of unsatisfactory retainability of a safe temperature on the skin surface to which the compress structure is applied.

Usually, a hot compress structure is applied directly to an affected part to treat neuralgia, etc. The user can perceive a change of temperature sensitively, and the temperature range required is extremely limited which is 38° to 44° C. Further, it is important that when applied to an affected part, the hot compress structure be capable of warming the whole of the affected part uniformly and that the heating composition in the hot compress structure should not be localized and hence not cause a sense of incongruity in use.

SUMMARY OF THE INVENTION

It is the object of the present invention to provide a hot compress structure capable of easily controlling the temperature to a predetermined level so that when it is used in close contact with the human body the skin temperature does not exceed a predetermined certain range. it is a further object of the present invention to provide a compress which maintains the required temperature for a sufficiently long time.

DESCRIPTION OF THE PREFERRED EMBODIMENT

Figure 1:
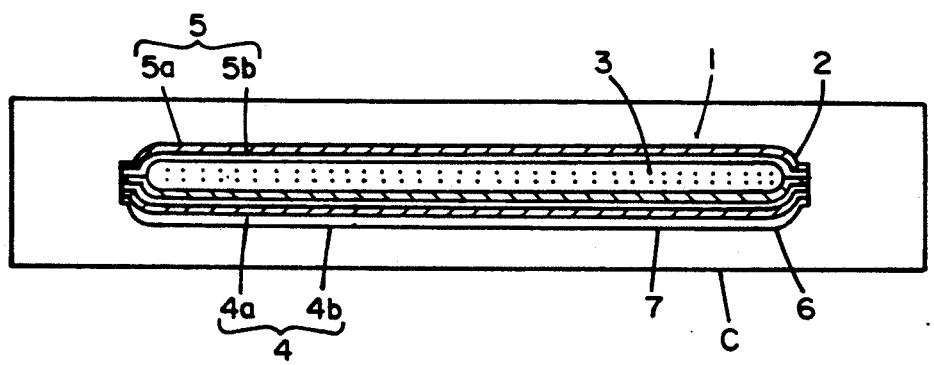
FIG. 1 is a sectional view of a hot compress structure according to an embodiment of the present invention.

According to the present invention there is provided a hot compress structure comprising a flat bag having no opening and having one surface constituted by a gas-permeable film, a heating composition capable of generating heat in the presence of air and sealed in the interior of the flat bag, and a compress layer being provided on the other surface of the flat bag. The amount of moisture permeated through the gas-permeable film is in the range of 100 to 400 $g/m^2.24$ hr as measured according to an ASTM method (E-96-80D method).

The heating composition generates heat by reacting with oxygen contained in the air introduced through the gas-permeable film, while the release of the heat is performed in the form of a rise in temperature of the heating composition and that of the compress layer, the resulting heat transfer, evaporative latent heat for converting water in the system into steam, and release of the steam to the exterior of the system through the gas-permeable film. By causing a balance between such generation and release of the heat, it becomes possible to maintain the temperature at a predetermined level over a long time. Having made studies, the present inventors found that in order to maintain a predetermined temperature it was important for the gas-permeable film to be air and steam permeable, but that in gas permeability, steam, rather than air, had a greater influence on realizing temperature characteristics superior in reproducibility. In other words, we found that the steam permeability, rather than air permeability, of the gas-permeable film had a direct bearing on the temperature characteristics of the hot compress structure.

This is presumed to be for the following reason. As the temperature of the hot compress structure rises, the evaporation of water contained in the heating composition becomes vigorous and the relative humidity in the bag reaches 100%. As a result, there occurs movement of steam from the interior to the exterior through the gas-permeable film. In this case, since the temperature outside the bag is lower than the internal temperature of the bag, part of the steam is adsorbed and condensed in the fine holes of the gas-permeable film, thereby causing a change in effective diameter of the fine holes contributing to the gas permeation in the film. Therefore, it is understood that the value of gas permeability of the gas-permeable film in the hot compress structure in use, that is, when the humidity is high, is greatly different from that in dry condition. Further, the larger the number and the smaller the diameter of the fine holes which contribute to the gas permeation in the film, the more outstanding the said effect, even between films having the same permeability for dry air, so the gas permeability of film in dry condition and that in wet condition are not in one-to-one correspondence. Therefore, as to the gas permeability of the gas-permeable film during use of the hot compress structure, the steam permeability is measured accurately as a practical value, not the air permeability measured in dry condition. This is considered to be the reason why the steam permeability serves as a direct index in the evaluation of characteristics of the hot compress structure.

The present invention has been accomplished on the basis of the above-mentioned technical idea, in which there is used a gas-permeable film having steam permeability controlled in a predetermined range, thereby permitting a desired temperature to be maintained over a long period of time. More specifically, there is used a gas-permeable film having a moisture permeability in the range of 100 to 400 $g/m^2.24$ hr as measured according to an ASTM method (E-96-80D method), whereby an affected part of the skin can be held for a long time at a temperature in the range of 38° to 44° C. which range is safe without causing a low-temperature burn and is suitable for a warming effect.

The above ASTM method (E-096-90D method) is the following method. 20 ml of pure water is poured into a cup having an inside diameter of 6.18 cm and a height of 1.5 cm, then the upper surface of the cup is closed with a gas-permeable film followed by fixing with wax, thereafter the thus-closed cup is allowed to stand for 24 hours in an atmosphere of constant temperature (32.2° C.) and constant humidity (50%). Then, the amount of water decreased in the cup is measured and the amount of water released (evaporated) is indicated in terms of (g/m$^2$.24 hr).

A moisture permeability of the gas-permeable film less than 100 g/m$^2$.24 hr is not desirable because the amount of heat generated will be too small, resulting in poor effect of hot fomentation, while a value thereof exceeding 400 g/m$^2$.24 hr is not desirable, either, because the temperature will rise and the maximum temperature may exceed 50° C., causing the danger of a low-temperature burn. Thus, the range of 150 to 350 g/m$^2$.24 hr is a most desirable range of moisture permeability of the gas-permeable film.

As the material resin of the gas-permeable film, it is desirable to select a resin having heat sealability and one that is capable of being thermally fused, easily. Examples are polyethylene, polypropylene, nylon, polyester, polyvinyl chloride, polyvinylidene chloride, polyurethane, polystyrene, a saponified ethylene-vinyl acetate copolymer, an ethylene-vinyl acetate copolymer, natural rubber, reclaimed rubber and synthetic rubber. Particularly, hydrophobic thermoplastic resins such as polyethylene and polypropylene are preferred.

For producing a gas-permeable film having a moisture permeability in the range of 100 to 400 g/m$^2$.24 hr, there may be adopted a suitable method capable of forming innumerable pores in the film. For example, any of the following methods can be used.

1) Sintering a fine resin powder into a porous film.
2) Melting and drawing a polyolefin resin, followed by heat treatment and re-drawing.
3) Incorporating liquid or a finely powdered solid into a resin, followed by forming into film and subsequent extraction of the incorporated liquid or solid.
4) Blending a finely powdered filler into a polyolefin resin, followed by melt-forming, and drawing the resulting film or sheet uni- or biaxially.

According to any of such conventional porous film forming methods, any person skilled in the art can easily form a film having a moisture permeability in the range of 100 to 400 g/m$^2$.24 hr. The film thickness is in the range of 1 to 300μ. Preferably 5 to 100μ.

A gas-permeable fabric or non-woven fabric may be laminated to the gas-permeable film to reinforce the latter. As such, a reinforcing fabric there may be used any of fabrics obtained using artificial fibers such as, for example, nylon, vinylon, polyester, rayon, acetate, acrylonitrile, polyethylene, polypropylene and polyvinyl chloride, or natural fibers such as, for example, cotton, hemp and silk. In this case, it is necessary to take care so that the moisture permeability of the gas-permeable film is not lost.

It is desirable for the gas-permeable film to have flexibility, preferably exhibiting a value not larger than 2.5 g on a loop stiffness tester. The use of such a gas-permeable film is advantageous in that when the heating composition absorbs oxygen it comes into close contact with the gas-permeable film, whereby the localization thereof can be prevented easily.

According to the loop stiffness tester, a sample is fixed in a loop form in a direction in which the sample is difficult to slacken by its own bending weight, and flexibility is measured in terms of the strength of stiffness based on a load required for crushing the loop in the diametrical direction thereof. It is said that the measured value thus obtained is least influenced by the weight of the sample itself. The measurement was made herein at a compressing rate of 3.5 mm/sec using a loop stiffness tester No. 581 manufactured by Toyo Seiki Seisakusho K. K.

As the heating source used in the present invention there may be used any conventional heating compositions provided they induce an exothermic reaction in the presence of air and contain water. A composition containing a metallic powder, a chloride and water as essential components is preferred. And particularly preferred is a composition comprising a metallic powder such as iron powder, an active carbon which induces an oxidation reaction with the metallic powder, adjusts pH and exhibits a catalytic action, a chloride such as sodium chloride for destroying the oxide film formed on the surface of the metallic powder to let the oxidation reaction of iron powder proceed smoothly, water, and a water retaining agent for eliminating stickiness caused by water.

For maintaining a desired temperature and shape retaining property stabily for a long time, the above heating composition preferably has the following proportions of components: iron 40-75 wt %, active carbon 1-10 wt %, sodium chloride 1-10 wt %, water 10-40 wt %, water retaining agent 1-40 wt %.

The heating composition is sealed uniformly into a flat bag, and the amount thereof to be sealed in the bag is preferably in the range of 500 to 7,000 g/m$^2$ in terms of the area of exposed surface of a fomentation base. If it is smaller than 500 g/m$^2$, it will be impossible to maintain a desired temperature over a long period of time, thus making it impossible to obtain a satisfactory hot fomentation effect. If it exceeds 7,000 g/m$^2$, it will become difficult to put the heating composition into the bag, or the hot compress structure may become too thick which not only results in deteriorated sense of use or portability but also is uneconomical and undesirable.

As the components of the heating composition, various components are available depending on how to produce and use, but any components used in a disposable pocket heater are employable irrespective of kind, shape and purity.

The water retaining agent is not specially limited if only it has a high water retaining property and is capable of eliminating the stickiness of the heating composition. Preferred examples are vermiculite, silica powder, wood powder and a water absorbing polymer.

In the hot compress structure of the present invention, a compress layer is provided on the side (background) opposite to the side where the gas-permeable film is provided in the flat bag with the heating composition sealed therein. The compress layer is for holding a fomentation such as water or a fomentation liquid or paste to stupe the skin. Usually, it comprises a fomentation holding member such as film or sheet and a fomentation base spread thereover.

The fomentation holding member may also serve as the background in the flat bag, or it may be laminated and bonded to the background using adhesion or melt-bonding means.

As the material for the film or sheet of the fomentation holding member, there may be used the same material as that used for the gas-permeable film.

Since the fomentation holding member is for holding a fomentation in an impregnated state, it is desirable to us, in addition to the above film and sheet, to use hydrophilic high polymers exhibiting capillarity such as, for example, paper, non-woven fabric, woven fabric and an open-cell sponge.

It is desirable that the compress layer be applicable to an affected part immediately after the application of a required fomentation base to the fomentation holding member according to purposes.

The application base is not especially limited, but preferably used in a fomentation liquid or a paste-like ointment containing a fomentation liquid.

In this way the fomentation base is applied and laminated to the fomentation holding member. It is desirable that the compress layer thus obtained should contain water to improve the heat transfer to the skin and be superior in stickiness. It is also desirable that at the time of heat generation the compress layer should soften at a temperature of 38°–44° C. and have a moderate agglomeratability to prevent the ointment in the compress layer from remaining on the skin. For example, as materials for hydrous purpose there may be used CMC, polysodium acrylate, water-absorbing resins, kaolin, gelatin and various crosslinking agents. In addition, various materials may be used for obtaining desired physical properties such as high flexibility and stickiness.

The fomentation liquid is not especially limited; those commonly used are employable such as, for example, water, hot spring water, aqueous sodium chloride solution, glycerin, peppermint oil, methyl salicylate and glycol salicylate, alone or in combination of two or more. Liquid alcohols and liquid aliphatic acid esters are also employable, in which there may be dissolved various substances, including those commonly used such as menthol, camphor and non-steroid agents, and also a surfactant may be incorporated as a dispersion stabilizer.

Preferably, the exposed surface of the fomentation base thus obtained is covered with a protective film.

In this way the fomentation base is laminated to the fomentation holding member and in this case, it is preferable that the amount of the fomentation base used be in the range of 400 to 2,500 grams per square meter of the exposed surface thereof. If it is smaller than 400 g/m$^2$, it will be impossible to form a uniform fomentation base layer, thus making it impossible to obtain an excellent hot fomentation effect, while if it exceeds 2,500 g/m$^2$, the rising of temperature after application will become slow, that is, the fomentation will become deficient in rapid action; besides, the hot compress structure will become thicker and too heavy, thus deteriorating the sense of use and portability, which is uneconomical.

The compress layer thus formed is lapped on the side of the flat bag opposite to the side on which is provided the gas-permeable film, then its peripheral portion is bonded by such means as adhesion, melt-bonding or sewing.

The present invention will be described below in more detail with reference to the accompanying drawings. FIG. 1 is a sectional view showing an embodiment of the present invention. it is to be understood that the invention is not limited thereto.

In FIG. 1, the reference numeral 1 denotes a hot compress structure embodying the present invention. The hot compress structure 1 comprises a flat bag 2 and a heating composition 3 sealed in the flat bag. The flat bag 2 has one surface constituted by a gas-permeable film 5a having a predetermined moisture permeability, with a reinforcing gas-permeable fabric 5b being laminated thereto, and is provided on the other surface thereof with a compress layer 4. The flat bag 2 has no opening.

The compress layer 4 is for holding water or a fomentation such as a fomentation liquid or paste to stupe the skin and it comprises a fomentation holding member 4a and a fomentation base 4b. The fomentation holding member 4a may also serve as the background (the side opposite to the gas-permeable film side) of the flat bag 2, or it may be laminated and bonded to the background by suitable means such as adhesion or melt-bonding.

It is preferably that the exposed surface of the fomentation base 4b be covered with a releasable protective film 7.

The compress layer 4 thus formed is lapped on the side of the flat bag 2 opposite to the side where the gas-permeable film 5a is provided, then its peripheral portion is bonded by suitable means such as adhesion, melt-bonding or sewing. In this case, one end of the peripheral portion is left open, and after the heating composition is put into the bag, it is sealed by the above means. In this way the hot compress structure is completed.

The hot compress structure 1 is sealed into a gas-tight bag C and then marketed.

In this case, the hot compress structure may be placed in the gas-tight bag alone or with additional compress structures together in folded stages so as to be cut freely according to purposes of use.

In using the hot compress structure 1 of the present invention having the above construction, it is taken out from the gas-tight bag C, then the protective film 7 is peeled off and the compress layer 4 is brought into close contact with an affected part.

OPERATION

Since the hot compress structure of the present invention has the foregoing construction, when it is applied to the human body, the reaction heat produced by an oxidation reaction of the heating composition in the hot compress structure with air, an evaporative latent heat of water in the heating composition, and the release of heat by blood circulation, are maintained in a well-balanced condition, so that the temperature is maintained in the desired temperature range over a long period of time.

Thus, the skin temperature is adjusted in the range of 38° C. to 44° C., and since there is no localization of the heating composition, the temperature distribution throughout the whole of the flat bag is maintained uniform.

EXAMPLES

The following examples are given to show effects of the hot compress structure of the present invention.

Examples 1–4 and Comparative Examples 1–2

Experiments were conducted using the hot compress structure illustrated in FIG. 1.

As a heating composition, an intimate mixture consisting of 60 wt % of iron powder, 3 wt % of active carbon, 3 wt % of NaCl, 3 wt % of a water retaining agent and 31 wt % of water was used. The area of a compress layer used was 120 mm×90 mm. 18 g of the heating composition was used. There was used a fomentation consisting of about 20 g of kaolin, about 3 g of starch acrylate, about 5 g of gelatin, about 1 g of sorbitan monolaurate, about 0.05 g of ethyl para-hydroxybenzoate, about 18 g of glycerin, about 45 g of water and about 1 g of titanium oxide. 8.7 g (810 g/m$^2$) of the fomentation was spread. Hot compress structures were prepared using gas-permeable polyethylene films different in moisture permeability. The moisture permeability of each such gas-permeable film was controlled in the following manner. An inorganic filler-containing polyethylene was melt-formed into films, then the films were subjected to different drawing conditions and part of the pores of the resulting films were melt-bonded.

The hot compress structures thus prepared were each taken out from a gas-tight bag and stuck onto the skin (waist), then changes in temperature of the skin (waist) were recorded using SBR 187-35CA (a product of Rika kogyo K.K.), using five thermocouples fixed on the skin (waist) side. The results are as set forth in Table I, which results are mean values obtained by applying the hot compress structures to the waists of ten panellers.

TABLE 1

Figure 2:
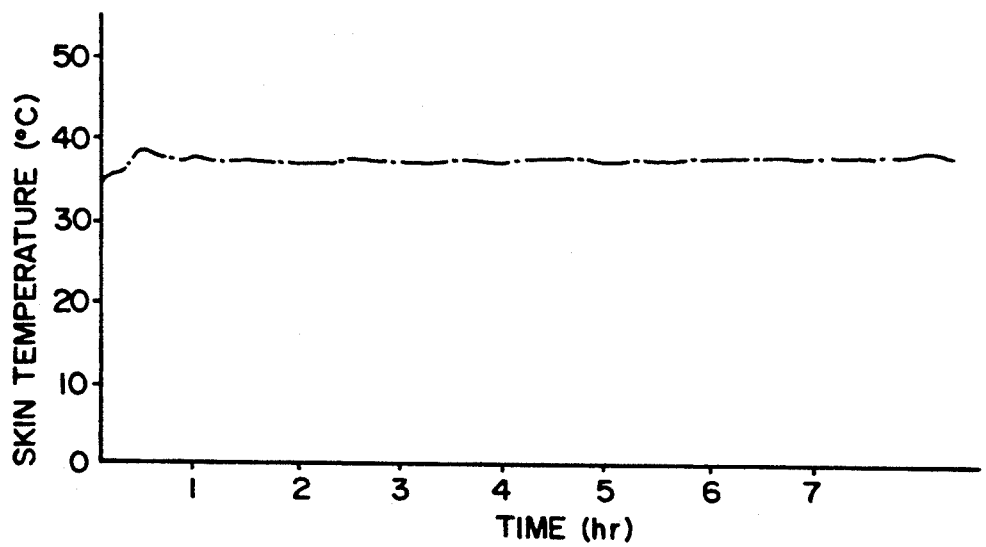
FIGS. 2 to 5 are temperature characteristic cut diagrams in the embodiment with varying values of moisture permeability.
Figure 3:
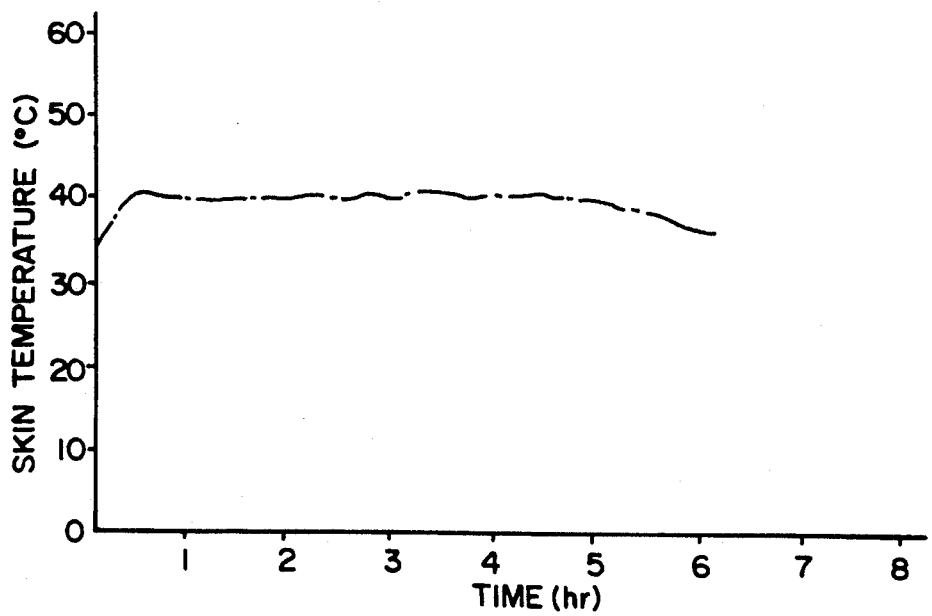
Figure 4:
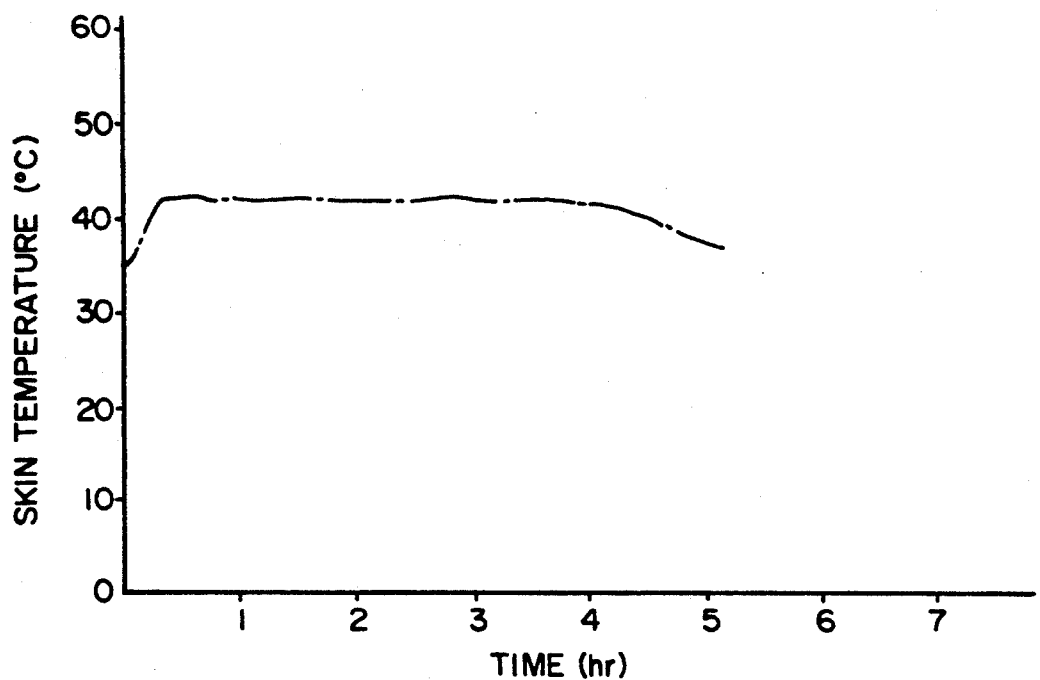
Figure 5:
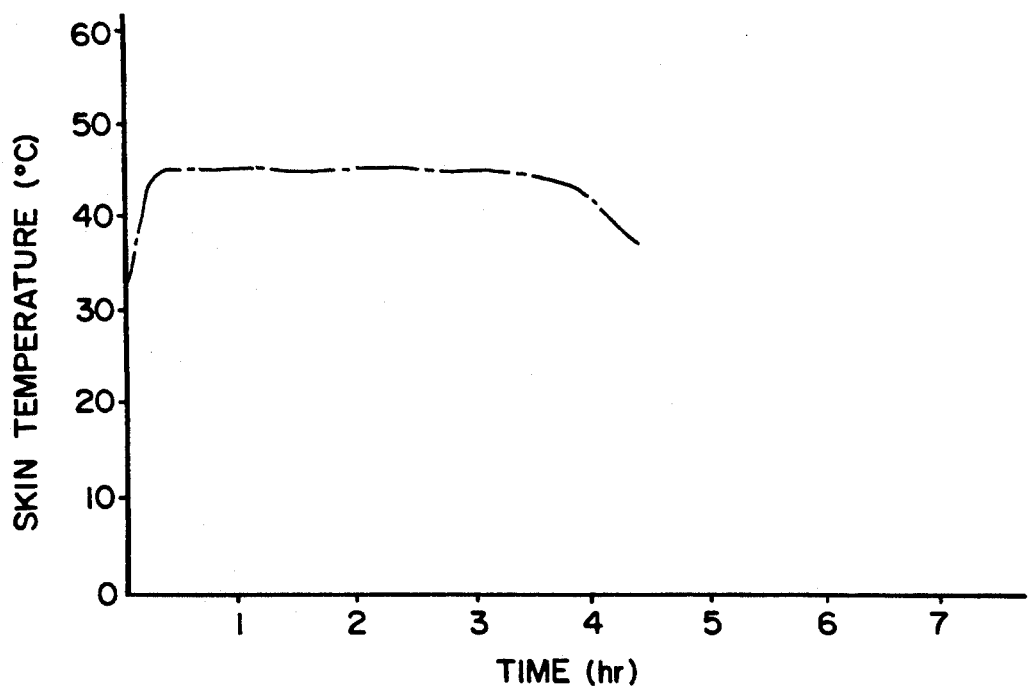
Figure 6:
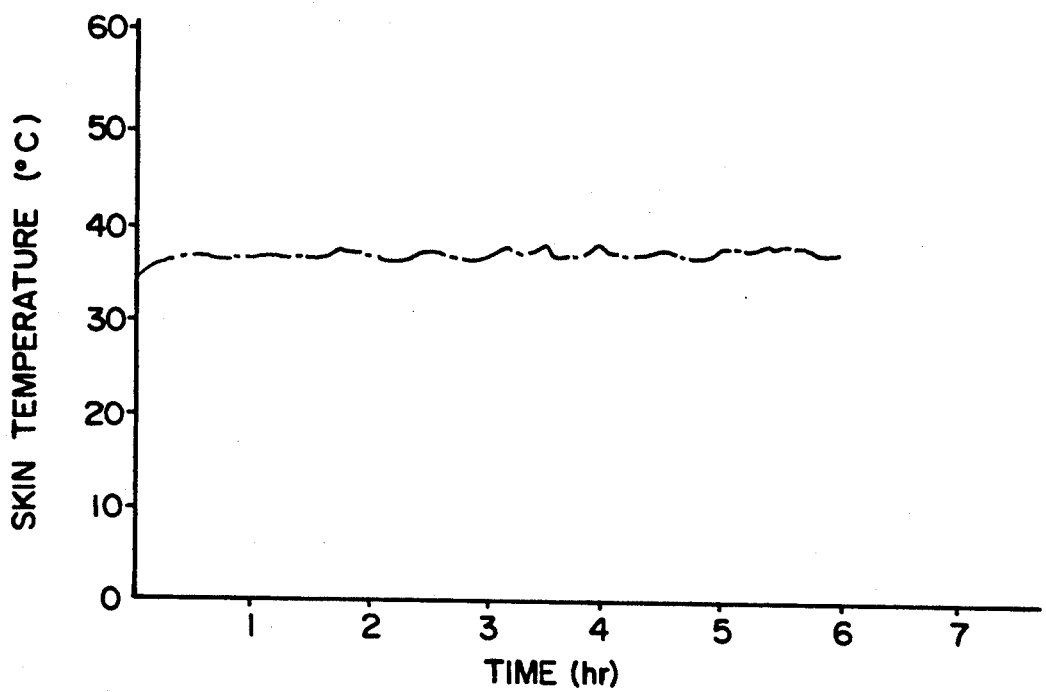
FIGS. 6 and 7 are temperature characteristic cut diagrams of comparative examples.
Figure 7:
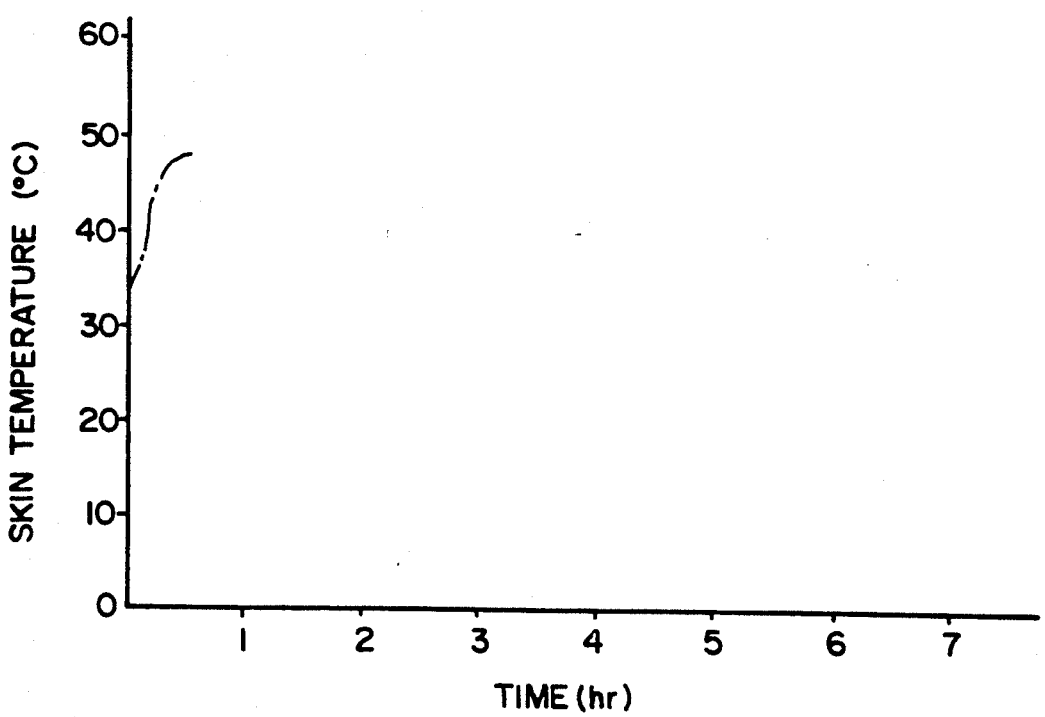

| Example | Moisture permeability (g/m$^2$·24 hr) | Temperature characteristic diagram |
|---|---|---|
| Example 1 | 110 | FIG. 2 |
| " 2 | 164 | FIG. 3 |
| " 3 | 212 | FIG. 4 |
| " 4 | 363 | FIG. 5 |
| Comparative Example 1 | 85 | FIG. 6 |
| Comparative Example 2 | 436 | FIG. 7 |

Moisture permeability: measured according to an ASTM method (E-96-80D method)

From the results shown in FIGS. 2 to 7, it is seen that the maximum skin temperature differs and the hot fomentation effect varies, depending on the moisture permeability of gas-permeable film.

For example, as shown in FIG. 6, at a moisture permeability of 85 g/m$^2$.24 hr, the hot fomentation effect is poor because the amount of heat generated is small, and the hot compress structure having such a moisture permeability is unemployable.

On the other hand, as shown in FIG. 7, when the moisture permeability exceeds 436 g/m$^2$.24 hr, the skin temperature reaches 48.5° C. in about 30 minutes after the application of the hot compress structure, as indicated by the temperature characteristic, and thereafter the heat rises too much to the extent of the measurement being infeasible by the panellers. Thus, there is the danger of a burn and the hot compress structure is not employable.

Figure 8:
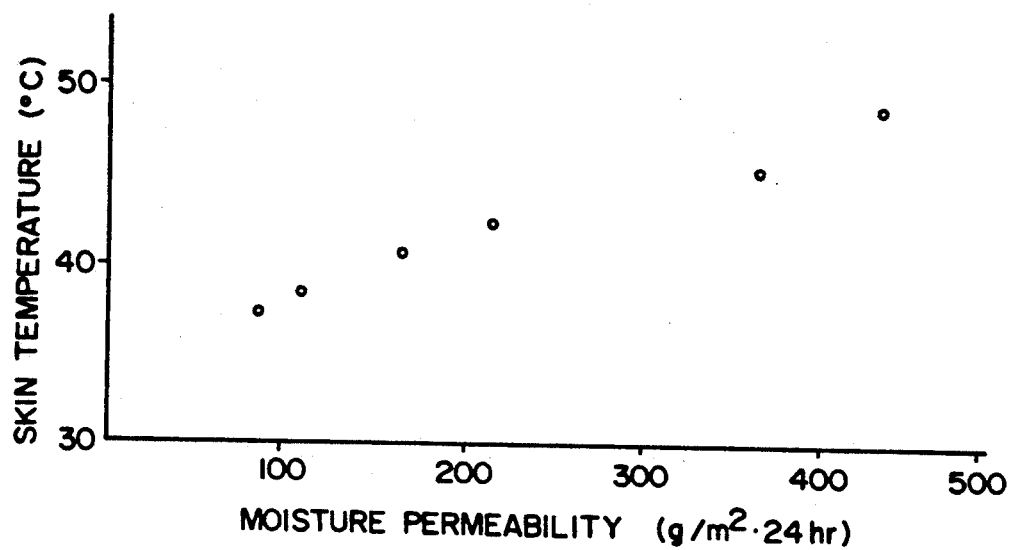
FIG. 8 is a characteristic cut diagram showing the relation between moisture permeability and maximum skin temperature.

In connection with the above experiments, FIG. 8 shows the relation between the moisture permeability and the maximum skin temperature.

From the above results, it is seen that when the moisture permeability is in the range of 100 to 400 g/m$^2$.24 hr, the skin temperature is controlled to a most suitable temperature in the range of 38° to 44° C. The duration of that temperature is as long as about 4 to 8 hours and is stable.

Example 5

Figure 9:
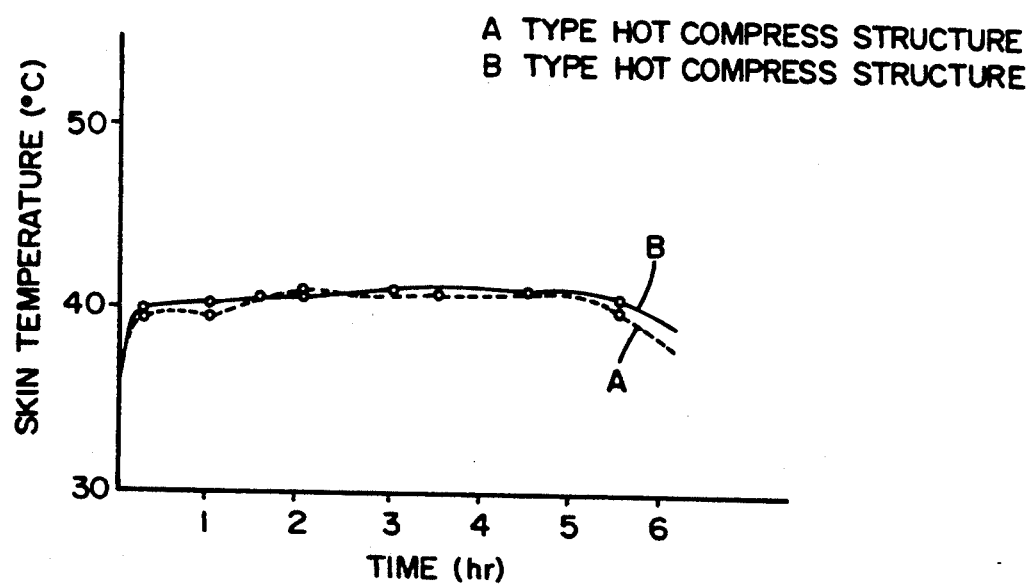
FIG. 9 is a characteristic diagram for the comparison of skin temperature between hot compress structures type A and type B when applied to the human body.

Hot compress structures were prepared in the same way as in Example 3 except using compress layer areas of 100 mm×70 mm (type A) and 130 mm×95 mm (type B) and amounts of the heating composition used of 11.7 g (1,670 g/m$^2$) (type A) and 20.6 g (1,670 g/m$^2$) (type B). Then, temperature characteristics were measured in the same manner as in Example 3. The results are as shown in FIG. 9.

Example 6

In place of the gas-permeable polyethylene film, there was used a gas-permeable polypropylene film in the same manner. There were obtained similar results.

From the above results, it is seen that when the hot compress structure is applied to the human body, even if the area of the compress layer is changed within the range not causing a sense of incongruity, the maximum skin temperature at the applied part does not change so greatly; therefor, with increase in area of a compress layer, the area of the skin where the hot compress structure is applied becomes larger, so that the movement of red cells in the human blood becomes active, thus accelerating blood circulation in a wide region and so affording an excellent hot fomentation effect.

EFFECT OF THE INVENTION

In the hot compress structure of the present invention there is used a gas-permeable film having a moisture permeability in the range of 100 to 400 g/m$^2$.24 hr, whereby the skin temperature can be controlled in a desired range, that is, a desired temperature can be maintained over a long period of time. Consequently, the present invention is effective in accelerating local blood circulation and improving the metabolizing function, so the effect of treating neuralgia, chronic rheumatism, lumbago and herpes is expected. Further, since there is no localization of the heating composition, the temperature distribution throughout the whole of the flat bag becomes uniform, causing no sense of incongruity when applied.

| | |
|---|---|
| 1 | hot compress structure |
| 2 | flat bag |
| 3 | heating composition |
| 4 | compress layer |
| 4a | hot fomentation holding member |
| 4b | fomentation base |
| 5 | gas-permeable film |
| 5a | gas-permeable base film |
| 5b | reinforcing gas-permeable fabric |
| C | gas-tight bag |

What is claimed is:

1. A hot compress structure comprising a flat bag with opposing flat surface having no opening and having one surface constituted by a gas-permeable film, and a heating composition capable of generating heat in the presence of air and sealed in the interior of the flat bag, with a compress layer that functions as a skin stupe and has a surface stickiness effective to cause the hot compress structure to stick to the skin of a human, said compress layer comprising a water containing fomentation layer and a fomentation base provided on the other surface of the flat bag, said gas-permeable film having a moisture permeability of 100 to 400 g/m$^2$.24 hr as measured according to ASTM method E-96-80D and said gas-permeable film, said heating composition and said compress layer, in combination, being effective to control the temperature of the skin in contact with the hot compress structure between about 38° and about 44° C.

2. A hot compress structure according to claim 1, wherein said heating composition contains a metallic powder, a chloride and water as essential components.

3. A hot compress structure according to claim 2, wherein said heating composition comprises 40-75 wt % of the metallic powder, 1-10 wt % of the chloride, 1-40 wt % of water, 1-10 wt % of an active carbon and 1-40 wt % of a water retaining agent.

4. A hot compress structure according to claim 2 or claim 3, wherein said metallic powder is an iron powder and said chloride is sodium chloride.

5. A hot compress structure according to claim 1, wherein said gas-permeable film is a hydrophobic thermoplastic resin film.

6. A hot compress structure according to claim 5, wherein said hydrophobic thermoplastic resin is a polyolefin.

7. A hot compress structure according to claim 6, wherein said polyolefin is polyethylene.

8. A hot compress structure according to claim 1, wherein the amount of said heating composition used is in the range of 500 to 700 g/m$^2$.

9. A hot compress structure according to claim 8 wherein said compress layer includes a fomentation base in an amount of 400-2,500 g/m$^2$.

10. A hot compress structure according to claim 1 including the following additional element:
   a releasable protective film covering the exposed exterior surface of the compress layer.

* * * * *